United States Patent [19]

Kaugars

[11] 4,014,932
[45] Mar. 29, 1977

[54] ALKYLTHIO BENZOIC ACID PHENYL-HYDRAZIDES

[75] Inventor: Girts Kaugars, Cooper Township, Kalamazoo County, Mich.

[73] Assignee: The Upjohn Company, Kalamazoo, Mich.

[22] Filed: Aug. 4, 1975

[21] Appl. No.: 601,502

Related U.S. Application Data

[62] Division of Ser. No. 530,085, Dec. 6, 1974, Pat. No. 3,931,318, which is a division of Ser. No. 54,622, July 13, 1970, Pat. No. 3,930,020.

[52] U.S. Cl. .................... 260/558 H; 260/558 S; 260/569
[51] Int. Cl.$^2$ ........................................ C07C 109/10
[58] Field of Search ......... 260/558 H, 558 P, 558 S

[56] References Cited

UNITED STATES PATENTS

| 2,767,173 | 10/1956 | Katz | 260/558 H X |
| 3,466,327 | 9/1969 | Tschesche et al. | 260/558 H X |
| 3,549,572 | 12/1970 | Minagawa et al. | 260/558 H X |
| 3,721,740 | 3/1973 | Folz | 424/327 |
| 3,829,488 | 8/1974 | Wolf et al. | 260/558 H X |

OTHER PUBLICATIONS

Boberg et al., Justus Liebigs Ann. Chem. 1970, 734, pp. 173-179.

Holland et al., J. Med. Chem. 6 (5), 519-524 (1963) (Chemicus Indicus Abstract 34073).

*Primary Examiner*—Daniel E. Wyman
*Assistant Examiner*—Thomas A. Waltz
*Attorney, Agent, or Firm*—William G. Jameson; Roman Saliwanchik; Sidney B. Williams

[57] ABSTRACT

Certain new ar or ar' (alkylthio) benzoyl chloride phenylhydrazones have been found to be anthelmintics and active against arthropod pests. The benzoyl ring and the phenylhydrazone ring can be otherwise substituted with, for example, halogen atoms, nitro groups, α-fluoroalkyl groups, other alkylthio groups, and alkyl groups. The new compounds are prepared by reacting an ar or ar' (alkylthio) benzoic acid 2-phenylhydrazide with phosphorus pentachloride to obtain an ar or ar' (alkylthio) benzoyl chloride (dichlorophosphinyl)-phenylhydrazone that is reacted with phenol to produce the desired ar or ar' (alkylthio) benzoyl chloride phenylhydrazones. Certain of the compounds can be prepared by direct halogenation of (alkylthio)benzaldehyde phenylhydrazone or an (alkylthio)benzoyl chloride phenylhydrazone. Methods of anti-arthropodal use and novel formulations for use are also described.

12 Claims, No Drawings

ALKYLTHIO BENZOIC ACID PHENYL-HYDRAZIDES

CROSS REFERENCE TO RELATED APPLICATION

This application is a division of my application Ser. No. 530,085, filed on Dec. 6, 1974 now U.S. Pat. No. 3,931,318, which is a division of my application Ser. No. 54,622, filed July 13, 1970 now U.S. Pat. No. 3,930,020.

SUMMARY OF THE INVENTION

This invention pertains to new chemical compounds, a new method for killing and controlling arthropod pests, and new formulations for suppressing the same. The invention is more particularly directed to new ar or ar' (alkylthio) benzoyl chloride phenylhydrazones, new ar or ar' (alkylthio) benzoic acid 2-phenylhydrazide starting compounds, a new method for killing and controlling arthropod pests with the new ar or ar' (alkylthio) benzoyl chloride phenylhydrazones, and new pest formulations containing the same.

The new ar or ar' (alkylthio) benzoyl chloride phenylhydrazones of this invention have the general structural formula:

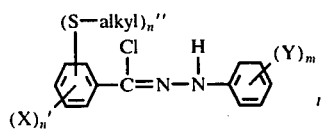

wherein "alkyl" is of from 1 to 6 carbon atoms, inclusive; X is halogen (i.e., bromine, chlorine, fluorine, and iodine), alkyl of from 1 to 6 carbon atoms, inclusive, alkylthio of from 1 to 6 carbon atoms, inclusive, $\alpha$-$F_n$alkyl of from 1 to 3 carbon atoms, inclusive, wherein $n$ is the integer 2 or 3, and nitro; Y is alkyl of from 1 to 6 carbon atoms, inclusive, halogen, alkylthio of from 1 to 6 carbon atoms, inclusive, $\alpha$-$F_n$alkyl of from 1 to 3 carbon atoms, inclusive, and nitro; $n''$ is one except when Y is alkylthio, when it can be zero; $n'$ is an integer 0 to 3, inclusive; and $m$ is an integer from 0 to 3, inclusive, the sum of $n'+n''+m$ being not more than 6, the sum of carbon atoms in the alkyl substituents being not more than 15, there being no more than one nitro group in the molecule, and no more than two $\alpha$-$F_n$alkyl groups on any benzene ring or three total.

DETAILED DESCRIPTION OF THE INVENTION

The new ar or ar' (alkylthio) benzoyl chloride phenylhydrazones of this invention are readily prepared by reacting a selected new ar or ar' (alkylthio) benzoic acid 2-phenylhydrazide starting compound with phosphorus pentachloride, reacting the resulting, corresponding new ar or ar' (alkylthio) benzoyl chloride (dichlorophosphinyl)phenylhydrazone with phenol, and recovering the desired new ar or ar' (alkylthio) benzoyl chloride phenylhydrazone. The process can be represented as follows:

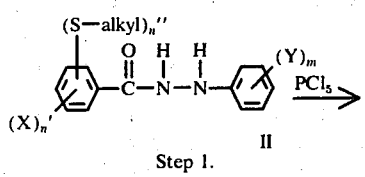

Step 1.

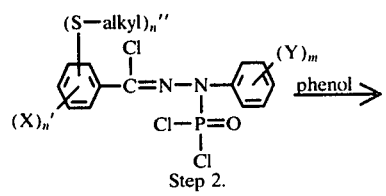

Step 2.

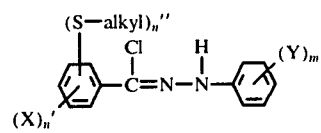

Step 1. of the foregoing process proceeds when a new ar or ar' (alkylthio) benzoic acid 2-phenylhydrazide starting compound (compounds of Formula II, above) and the phosphorus pentachloride are mixed in the presence of a reaction medium at a temperature in the range of about 10° C. up to about the boiling point of the reaction medium. Higher and lower temperatures can be used, however. The reaction rate will be decreased at low temperatures, and a pressure vessel would be needed to effect reaction temperatures above the boiling point at atmospheric pressure. In accordance with a preferred embodiment, the initial reaction mixture is heated.

Appropriate reaction media include, for example, the chlorinated hydrocarbon solvents, aliphatic or aromatic hydrocarbon solvents, and ethers. Representative specific ones are carbon tetrachloride (preferred), methylene chloride, chloroform, 1,2-dichloroethylene, benzene, toluene, technical hexane, diethyl ether, and dioxane.

The process can be practiced without isolating the new ar or ar' (alkylthio) benzoyl chloride (dichlorophosphinyl)phenylhydrazone intermediate when three equivalents or more of phenol are added to the initial reaction mixture after it has been cooled to about 0° to 25° C. The phenol reacts with the new ar or ar' (alkylthio) benzoyl chloride (dichlorophosphinyl)phenylhydrazone intermediate to produce triphenyl phosphate, and the desired new ar or ar' (alkylthio) benzoyl chloride phenylhydrazone is then recovered and purified by conventional methods. The solvent medium is removed by evaporation, and the desired product is recovered, e.g., by filtration from the residual triphenyl phosphate or by chromatographic techniques. The compound is purified by recrystallization.

The new ar or ar' (alkylthio) benzoic acid 2-phenylhydrazide starting compounds of Formula II can be readily prepared by known methods. According to one method an (alkylthio) benzoyl chloride is reacted with a phenylhydrazine as described by J. Hausknecht, Chem. Ber. 22, p. 324 (1889), and E. Bamberger and W. Pemsel, Chem. Ber. 36, p. 359 (1903). Another method is described in U.S. Pat. No. 2,912,461, issued Nov. 10, 1959, that utilizes a benzoate ester and a phenylhydrazine. Still another method described by W. Autenrieth and G. Thomae, Chem. Ber. 57, p. 423 (1924) reacts a benzoic acid anhydride with a phenylhydrazine to produce the corresponding benzoic acid 2-phenylhydrazide. The Examples hereinafter illustrate conventional methods for making (alkylthio) benzoic acid 2-phenylhydrazide and benzoic acid 2-(alkylthiophenyl)hydrazide intermediates for starting compounds. The various (alkylthio) benzoyl chloride (substituted-phenyl)hydrazine and [(alkylthio)phenyl]hydrazine starting compounds are prepared according to conventional methods.

The new anti-arthropodal ar or ar' (alkylthio) benzoyl chloride phenylhydrazones of this invention (compounds according to Formula I) can also be prepared by chlorinating an ar or ar' (alkylthio) benzaldehyde phenylhydrazone. Chlorination of an ar or ar' (alkylthio)benzaldehyde phenylhydrazone can be accomplished as described by J. E. Humphries, H. Humble and R. Evans, J. Chem. Soc. 127, p. 1304 (1925). But this chlorination is of limited usefulness when the starting ar or ar' (alkylthio)benzaldehyde phenylhydrazone has unsubstituted active sites that will yield to chlorination at positions on the phenylhydrazone portion that are desired to remain unsubstituted in a particular instance. Direct chlorination of an (alkylthio)benzaldehyde phenylhydrazone is an effective way of producing (alkylthio)benzoyl chloride (2,4,6-trichlorophenyl)hydrazone.

Still another method described by L. A. Jones, C. K. Hancock, and R. B. Seligman, J. Org. Chem. 26, p. 228 (1961) can be used. The described method utilized $\alpha,\alpha,\alpha$-trichlorotoluene and 2,4-dinitrophenylhydrazine to produce benzoyl chloride 2,4-dinitrophenylhydrazone. The new compounds of this invention can be prepared in the same manner.

Example 1

Preparation of p-(Methylthio)benzoyl Chloride Phenylhydrazone

Part A - p-(Methylthio)benzoic Acid 2-phenylhydrazide

A mixture consisting of 21.88 g. (0.130 mole) p-(methylthio)benzoic acid and 25 ml. thionyl chloride was heated at the reflux temperature until evolution of gas ceased and a clear solution was obtained. After removing the excess thionyl chloride on a rotary evaporator and then under substantially complete vacuum, the solid residue that remained was dissolved in 35 ml. dioxane. The dioxane solution was mixed with a solution consisting of 14.06 g. (0.130 mole) phenylhydrazine in 100 ml. pyridine initially at 5° to 10° C. Inadvertently, about one third of the acid chloride was added rapidly and the mixture was heated to 31° C. by the exothermic reaction. The reaction mixture was set aside at 25° C. with continuous stirring for 3 days. It was then poured into 1.5 l. water in order to precipitate the desired p-(methylthio)benzoic acid 2-phenylhydrazide. The precipitate was collected on a filter, washed with water, washed with 1N hydrochloride acid, and finally washed with water. The washed filter cake was then recrystallized from 3A alcohol to give 23.2 g. (69% yield) of p-(methylthio)benzoic acid 2-phenylhydrazide having a melting point at 165.5° to 167.5° C. Recrystallization from 250 ml. ethyl acetate gave the compound melting at 167° to 168° C. (shrinks at 162° C.). Two further recrystallizations from ethyl acetate gave the compound melting at 167° to 168.5° C. with shrinkage at 161.5° C.

Analysis:
Calc'd. for $C_{14}H_{14}N_2OS$:
C, 65.09; H, 5.46; N, 10.84; S, 12.41.
Found: C, 64.80; H, 5.57; N, 10.80; S, 12.34.

Part B -p-(Methylthio)benzoyl Chloride Phenylhydrazone

A mixture consisting of 14.2 g. (0.068 mole) phosphorus pentachloride, 100 ml. carbon tetrachloride, and 16.78 g. (0.065 mole) p-(methylthio)benzoic acid 2-phenylhydrazide (prepared in Part A above) was reacted at 25° C. until evolution of gas ceased. The reaction mixture was then heated to the reflux temperature and a clear solution resulted. The solution was chilled in ice and a suspension of 20.7 g. (0.22 mole) phenol in 50 ml. carbon tetrachloride was added. After removing the carbon tetrachloride by evaporation on a rotary evaporator at 31° C. the resulting suspension of product in triphenylphosphate was filtered. The filter cake was washed with technical hexane (Skellysolve B, a mixture of isomeric hexanes having a boiling range between 146° and 156° Fahrenheit), and then was washed with diethyl ether. Crystallization from 75 ml. ethyl acetate gave 8.10 g. (44.9% yield) of p-(methylthio)benzoyl chloride phenylhydrazone having a melting point of 138.5° to 142.5° C. Recrystallization from a mixture of ethyl acetate and the Skellysolve B gave the compound with the same melting point.

Analysis:
Calc'd. for $C_{14}H_{13}ClN_2S$:
C, 60.75; H, 4.73; Cl, 12.81; N, 10.12; S, 11.59.
Found: C, 60.41; H, 4.76; Cl, 12.75; N, 10.02; S, 11.51.

EXAMPLE 2

Preparation of Benzoyl Chloride [p-(Methylthio)phenyl]hydrazone

Part A - Benzoic Acid 2-[p-(Methylthio)phenyl]hydrazide

After dispersing and suspending 19.15 g. (0.100 mole) [p-(methylthio)phenyl]hydrazine hydrochloride in 500 ml. benzene, 10.1 g. (0.100 mole) triethylamine was added. The resulting suspension was stirred for 2 hrs. at 25° C. After adding 22.6 g. (0.100 mole) benzoic anhydride, the reaction mixture was heated at the reflux temperature for 4 hrs. The benzene was then removed by evaporation, and the residue thus obtained was washed once with water, twice with aqueous sodium bicarbonate, and finally with water. The washed residue was recrystallized once from 3A alcohol and once from a mixture of cyclohexane and ethyl acetate to give 15.0 g. (57.9% yield) of benzoic acid 2-[p-(methylthio)phenyl]hydrazide having a melting point at 139° to 140° C.

Analysis:
Calc'd. for $C_{14}H_{14}N_2OS$:
C, 65.08; H, 5.46; N, 10.85.
Found: C, 65.01; H, 5.70; N, 10.59.

Part B - Benzoyl Chloride [p-(Methylthio)phenyl]hydrazone

A mixture consisting of 7.9 g. (0.038 mole) phosphorus pentachloride, 100 ml. carbon tetrachloride, and 9.05 g. (0.035 mole) benzoic acid 2-[p-(methylthio)-phenyl]hydrazide (prepared in Part A above) was heated at the reflux temperature until evolution of gas ceased. The reaction mixture was chilled in ice, and a suspension of 11.3 g. (0.12 mole) phenol in 50 ml. carbon tetrachloride was added. After removing the carbon tetrachloride by evaporation under reduced pressure, the resulting triphenylphosphate solution of the desired product was poured through a column of silica gel. The column was eluted with a mixture of 1 part benzene and 1 part Skellysolve B. After removing the solvents from the eluate by evaporation under reduced pressure, the residue was recrystallized two times from cyclohexane to give benzoyl chloride [p-(methylthio)phenyl]hydrazone having a melting point at 94° to 95° C.

Analysis:
Calc'd. for $C_{14}H_{13}ClN_2S$: C, 60.75; H, 4.73; Cl, 12.81; N, 10.12;
S, 11.59.
Found: C, 60.77; H, 5.00; Cl, 13.08; N, 10.07;
S, 11.37.

EXAMPLE 3

Preparation of o-(Methylthio)-chlorobenzoyl Chloride Phenylhydrazone

Part A - o-(Methylthio)benzoic Acid 2-Phenylhydrazide to a solution consisting of 23.2 g. (0.214 mole) phenylhydrazine and 150 ml. pyridine was added a chilled solution consisting of 40.0 g. (0.214 mole) o-(methylthio)benzoyl chloride and 200 ml. dioxane. This reaction mixture was set aside at 25° for 2 days. It was then poured into 2.5 l. water in order to precipitate the desired product. The precipitate was collected on a filter and washed with water, with 1N aqueous hydrochloric acid, and finally with water. The washed filter cake was recrystallized from 3A alcohol to give 36.8 g. (66.5% yield) of o-(methylthio)benzoic acid 2-phenylhydrazide having a melting point at 127° to 128° C.

Analysis:
Calc'd. for $C_{14}H_{14}N_2OS$:
N, 10.84; S, 12.41.
Found: N, 10.75; S, 11.98.

Part B - o-(Methylthio)-chlorobenzoyl Chloride Phenylhydrazone

A mixture consisting of 21.9 g. (0.105 mole) phosphorus pentachloride, 150 ml. of carbon tetrachloride, and 25.83 g. (0.100 mole) o-(methylthio)benzoic acid 2-phenylhydrazide (prepared in Part A above) was heated at the reflux temperature until evolution of hydrogen chloride ceased. The reaction mixture was chilled in an ice-bath, and a suspension of 31.5 g. (0.335 mole) phenol in 50 ml. carbon tetrachloride was added. After removing the carbon tetrachloride by evaporation under reduced pressure, the resulting triphenylphosphate solution of the desired product was poured through a column of silica gel. Elution was effected with a mixture consisting of 1 part benzene and 1 part Skellysolve B. After removing the solvents from the eluate by evaporation under reduced pressure, 2.0 g. of residue was obtained. Recrystallization from petroleum ether gave an o-(methylthio)-chlorobenzoyl chloride phenylhydrazone having a melting point at 65° to 66.5° C.

Analysis:
Calc'd. for $C_{14}H_{12}Cl_2N_2S$:
C, 54.02; H, 3.89; Cl, 22.78; N, 9.00; S, 10.30.
Found: C, 54.09; H, 3.76; Cl, 22.77; N, 9.02; S, 10.34.

EXAMPLE 4

Preparation of p-(Methylthio)benzoyl Chloride (2,4-Dibromophenyl)hydrazone

To an ice-cold solution of 5.0 g. (0.018 mole) p-(methylthio)benzoyl chloride phenylhydrazone in 200 ml. carbon tetrachloride is added 7.2 g. (0.045 mole) bromine dissolved in 25 ml. carbon tetrachloride. The solution is heated at the reflux temperature for 4 hrs., and then the carbon tetrachloride is removed by evaporation under reduced pressure. The residue thus obtained is recrystallized to give the desired p-(methylthio)benzoyl chloride (2,4-dibromophenyl)hydrazone.

EXAMPLE 5

Following the procedure of Example 1, Part A, but substituting
3-fluoro-4-(methylthio)benzoic acid,
m-(methylthio)benzoic acid,
p-(ethylthio)benzoic acid,
p-(isopropylthio)benzoic acid,
p-(n-hexylthio)benzoic acid,
2,6-dichloro-4-(methylthio)benzoic acid,
3-iodo-4-(methylthio)benzoic acid,
2-bromo-4-(methylthio)benzoic acid,
2-bromo-5-chloro-4-(methylthio)benzoic acid,
2-methyl-4-(methylthio)benzoic acid,
3-ethyl-5-(ethylthio)benzoic acid,
3-(n-hexyl)-4-(methylthio)benzoic acid,
3-isopropyl-5-(methylthio)benzoic acid,
2-chloro-4-methyl-5-(methylthio)benzoic acid,
2,6-dibromo-3-ethyl-5-(methylthio)benzoic acid,
3-(methylthio)-4-nitrobenzoic acid,
3-(methylthio)-5-trifluoromethyl benzoic acid,
2-($\alpha,\alpha$-difluoroethyl)-4-(methylthio)benzoic acid,
3,5-di(methylthio)benzoic acid,
2,3,5-tri(methylthio)benzoic acid,
3-bromo-2-nitro-5-(methylthio)benzoic acid, and
2-chloro-5-(n-hexylthio)benzoic acid for p-(methylthio)benzoic acid there is prepared
3-fluoro-4-(methylthio)benzoic acid 2-phenylhydrazide,
m-(methylthio)benzoic acid 2-phenylhydrazide,
p-(ethylthio)benzoic acid 2-phenylhydrazide,
p-(isopropylthio)benzoic acid 2-phenylhydrazide,
p-(n-hexylthio)benzoic acid 2-phenylhydrazide,
2,6-dichloro-4-(methylthio)benzoic acid 2-phenylhydrazide,
3-iodo-4-(methylthio)benzoic acid 2-phenylhydrazide,
2-bromo-4-(methylthio)benzoic acid 2-phenylhydrazide,
2-bromo-5-chloro-4-(methylthio)benzoic acid 2-phenylhydrazide,
2-methyl-4-(methylthio)benzoic acid 2-phenylhydrazide,
3-ethyl-5-(ethylthio)benzoic acid 2-phenylhydrazide,
3-(n-hexyl)-4-(methylthio)benzoic acid 2-phenylhydrazide,
3-isopropyl-5-(methylthio)benzoic acid 2-phenylhydrazide,
2-chloro-4-methyl-5-(methylthio)benzoic acid 2-phenylhydrazide,
2,6-dibromo-3-ethyl-5-(methylthio)benzoic acid 2-phenylhydrazide,
3-(methylthio)-4-nitrobenzoic acid 2-phenylhydrazide, 3-(methylthio)-5-trifluoromethylbenzoic acid 2-phenylhydrazide,
2-(α,α-difluoroethyl)-4-(methylthio)benzoic acid 2-phenylhydrazide,
3,5-di(methylthio)benzoic acid 2-phenylhydrazide,
2,3,5-tri(methylthio)benzoic acid 2-phenylhydrazide,
3-bromo-2-nitro-5-(methylthio)benzoic acid 2-phenylhydrazide, and
2-chloro-5-(n-hexylthio)benzoic acid 2-phenylhydrazide, respectively.

EXAMPLE 6

Following the procedure of Example 2, Part A, but substituting
[3-bromo-5-(methylthio)phenyl]hydrazine,
[3-chloro-5-(methylthio)phenyl]hydrazine,
[4-ethyl-2-(methylthio)phenyl]hydrazine,
[2,6-diiodo-4-(methylthio)phenyl]hydrazine,
[3,5-di(methylthio)phenyl]hydrazine,
[p-(n-hexylthio)phenyl]hydrazine, for [p-(methylthio)phenyl]hydrazine and
p-(methylthio)benzoic anhydride and (p-bromophenyl)hydrazine,
m-(methylthio)benzoic anhydride and (p-chlorophenyl)hydrazine,
m-(methylthio)benzoic anhydride and (p-nitrophenyl)hydrazine,
m-(methylthio)benzoic anhydride and (2,4-diiodophenyl)hydrazine,
m-(methylthio)benzoic anhydride and (p-ethylphenyl)hydrazine,
m-(methylthio)benzoic anhydride and (m-isopropylphenyl)hydrazine,
m-(methylthio)benzoic anhydride and [m-(n-hexyl)phenyl]hydrazine,
m-(methylthio)benzoic anhydride and [p-(trifluoromethyl)phenyl]hydrazine,
m-(methylthio)benzoic anhydride and (2-chloro-4-nitrophenyl)hydrazine,
m-(methylthio)benzoic anhydride and (3-methyl-4-nitrophenyl)hydrazine,
m-(methylthio)benzoic anhydride and [3-methyl-5-(trifluoromethyl)phenyl]hydrazine,
m-(methylthio)benzoic anhydride and [p-(methylthio)phenyl]hydrazine,
m-(methylthio)benzoic anhydride and [3-(methylthio)-5-(trifluoromethyl)phenyl]hydrazine,
m-(methylthio)benzoic anhydride and (p-fluorophenyl)hydrazine and
3-(methylthio)-5-(n-hexyl)benzoic anhydride and [3,5-din-butyl-4-(methylthio)phenyl]hydrazine,
for the benzoic anhydride and [p-(methylthio)phenyl]hydrazine, respectively, there is prepared
benzoic acid 2-[3-bromo-5-(methylthio)phenyl]hydrazide,
benzoic acid 2-[3-chloro-5-(methylthio)phenyl]hydrazide,
benzoic acid 2-[4-ethyl-2-(methylthio)phenyl]hydrazide,
benzoic acid 2-[2,6-diiodo-4-(methylthio)phenyl]hydrazide,
benzoic acid 2-[3,5-di(methylthio)phenyl]hydrazide,
benzoic acid 2-[p-(n-hexylthio)phenyl]hydrazide,
p-(methylthio)benzoic acid 2-(p-bromophenyl)hydrazide,
m-(methylthio)benzoic acid 2-(p-chlorophenyl)hydrazide,
m-(methylthio)benzoic acid 2-(p-nitrophenyl)hydrazide,
m-(methylthio)benzoic acid 2-(2,4-diiodophenyl)hydrazide,
m-(methylthio)benzoic acid 2-(p-ethylphenyl)hydrazide,
m-(methylthio)benzoic acid 2-(m-isopropylphenyl)hydrazide,
m-(methylthio)benzoic acid 2-[m-(n-hexyl)phenyl]hydrazide,
m-(methylthio)benzoic acid 2-[p-(trifluoromethyl)phenyl]hydrazide,
m-(methylthio)benzoic acid 2-(2-chloro-4-nitrophenyl)hydrazide,
m-(methylthio)benzoic acid 2-(3-methyl-4-nitrophenyl)hydrazide,
m-(methylthio)benzoic acid 2-[3-methyl-5-[trifluoromethyl)phenyl]hydrazide,
m-(methylthio)benzoic acid 2-[p-(methylthio)phenyl]hydrazide,
m-(methylthio)benzoic acid 2-[3-(methylthio)-5-(trifluoromethyl)phenyl]hydrazide,
m-(methylthio)benzoic acid 2-(p-fluorophenyl)hydrazide, and
3-(methylthio)-5-(n-hexyl)benzoic acid 2-[3,5-di-n-butyl-4-(methylthio)phenyl]hydrazide, respectively.

EXAMPLE 7

Following the procedure of Example 1, Part B, but substituting
3-fluoro-4-(methylthio)benzoic acid 2-phenylhydrazide,
m-(methylthio)benzoic acid 2-phenylhydrazide,
p-(ethylthio)benzoic acid 2-phenylhydrazide,
p-(isopropylthio)benzoic acid 2-phenylhydrazide,
p-(n-hexylthio)benzoic acid 2-phenylhydrazide,
2,6-dichloro-4-(methylthio)benzoic acid 2-phenylhydrazide,
3-iodo-4-(methylthio)benzoic acid 2-phenylhydrazide,
2-bromo-4-(methylthio)benzoic acid 2-phenylhydrazide,
2-bromo-5-chloro-4-(methylthio)benzoic acid 2-phenylhydrazide,
2-methyl-4-(methylthio)benzoic acid 2-phenylhydrazide,
3-ethyl-5-(ethylthio)benzoic acid 2-phenylhydrazide,
3-(n-hexyl)-4-(methylthio)benzoic acid 2-phenylhydrazide,
3-isopropyl-5-(methylthio)benzoic acid 2-phenylhydrazide,
2-chloro-4-methyl-5-(methylthio)benzoic acid 2-phenylhydrazide,
2,6-dibromo-3-ethyl-5-(methylthio)benzoic acid 2-phenylhydrazide,
3-(methylthio)-4-nitrobenzoic acid 2-phenylhydrazide,
3-(methylthio)-5-trifluoromethylbenzoic acid 2-phenylhydrazide,
2-(α,α-difluoroethyl)-4-(methylthio)benzoic acid 2-phenylhydrazide,
3,5-di(methylthio)benzoic acid 2-phenylhydrazide,
2,3,5-tri(methylthio)benzoic acid 2-phenylhydrazide, 3-bromo-2-nitro-5-(methylthio)benzoic acid 2-phenylhydrazide,
2-chloro-5-(n-hexylthio)benzoic acid 2-phenylhydrazide, benzoic acid 2-[3-bromo-5-(methylthio)phenyl]hydrazide,
benzoic acid 2-[3-chloro-5-(methylthio)phenyl]hydrazide,
benzoic acid 2-[4-ethyl-2-(methylthio)phenyl]hydrazide,
benzoic acid 2-[2,6-diiodo-4-(methylthio)phenyl]hydrazide,
benzoic acid 2-[3,5-di(methylthio)phenyl]hydrazide,
benzoic acid 2-[p-(n-hexylthio)phenyl]hydrazide,
p-(methylthio)benzoic acid 2-(p-bromophenyl)hydrazide,
m-(methylthio)benzoic acid 2-(p-chlorophenyl)hydrazide,
m-(methylthio)benzoic acid 2-(p-nitrophenyl)hydrazide,
m-(methylthio)benzoic acid 2-(2,4-diiodophenyl)hydrazide,
m-(methylthio)benzoic acid 2-(p-ethylphenyl)hydrazide,
m-(methylthio)benzoic acid 2-(m-isopropylphenyl)hydrazide,
m-(methylthio)benzoic acid 2-[m-(n-hexyl)phenyl]hydrazide,
m-(methylthio)benzoic acid 2-[p-(trifluoromethyl)phenyl]hydrazide,
m-(methylthio)benzoic acid 2-(2-chloro-4-nitrophenyl)hydrazide,
m-(methylthio)benzoic acid 2-(3-methyl-4-nitrophenyl)hydrazide,
m-(methylthio)benzoic acid 2-[3-methyl-5-(trifluoromethyl)phenyl]hydrazide,
m-(methylthio)benzoic acid [p-(methylthio)phenyl]hydrazide,
m-(methylthio)benzoic acid 2-[3-(methylthio)-5-(trifluoromethyl)phenyl]hydrazide,
m-(methylthio)benzoic acid 2-(p-fluorophenyl)hydrazide, and
3-methylthio-5-(n-hexyl)benzoic acid 2-[3,5-di-n-butyl-4-(methylthio)phenyl]hydrazide for p-(methylthio)benzoic acid 2-phenylhydrazide, there are prepared
3-fluoro-4-(methylthio)benzoyl chloride phenylhydrazone,
m-(methylthio)benzoyl chloride phenylhydrazone,
p-(ethylthio)benzoyl chloride phenylhydrazone,
p-(isopropylthio)benzoyl chloride phenylhydrazone,
p-(n-hexylthio)benzoyl chloride phenylhydrazone,
2,6-dichloro-4-(methylthio)benzoyl chloride phenylhydrazone,
3-iodo-4-(methylthio)benzoyl chloride phenylhydrazone,
2-bromo-4-(methylthio)benzoyl chloride phenylhydrazone,
2-bromo-5-chloro-4-(methylthio)benzoyl chloride phenylhydrazone,
2-methyl-4-(methylthio)benzoyl chloride phenylhydrazone,
3-ethyl-5-(ethylthio)benzoyl chloride phenylhydrazone,
3-(n-hexyl)-4-(methylthio)benzoyl chloride phenylhydrazone,
3-isopropyl-5-(methylthio)benzoyl chloride phenylhydrazone,
2-chloro-4-methyl-5-(methylthio)benzoyl chloride phenylhydrazone,
2,6-dibromo-3-ethyl-5-(methylthio)benzoyl chloride phenylhydrazone,
3-(methylthio)-4-nitrobenzoyl chloride phenylhydrazone,
3-(methylthio)-5-tifluoromethylbenzoyl chloride phenylhydrazone,
2-(α,α-difluoroethyl)-4-(methylthio)benzoyl chloride phenylhydrazone,
3,5-di(methylthio)benzoyl chloride phenylhydrazone,
2,3,5-tri(methylthio)benzoyl chloride phenylhydrazone,
3-bromo-2-nitro-5-(methylthio)benzoyl chloride phenylhydrazone,
2-chloro-5-(n-hexylthio)benzoyl chloride phenylhydrazone,
benzoyl chloride 2-[3-bromo-5-(methylthio)phenyl]hydrazone,
benzoyl chloride 2-[3-chloro-5-(methylthio)phenyl]hydrazone,
benzoyl chloride 2-[4-ethyl-2-(methylthio)phenyl]hydrazone,
benzoyl chloride 2-[2,6-diiodo-4-(methylthio)phenyl]hydrazone,
benzoyl chloride 2-[3,5-di)methylthio)phenyl]hydrazone,
benzoyl chloride 2-[p-(n-hexylthio)phenyl]hydrazone,
p-(methylthio)benzoyl chloride (p-bromophenyl)hydrazone,
m-(methylthio)benzoyl chloride (p-chlorophenyl)hydrazone,
m-(methylthio)benzoyl chloride (p-nitrophenyl)hydrazone,
m-(methylthio)benzoyl chloride (2,4-diiodophenyl)hydrazone,
m-(methylthio)benzoyl chloride (p-ethylphenyl)hydrazone,
m-(methylthio)benzoyl chloride (m-isopropylphenyl)hydrazone,
m-(methylthio)benzoyl chloride [m-(n-hexyl)phenyl]hydrazone,
m-(methylthio)benzoyl chloride [p-(trifluoromethyl)phenyl]hydrazone,
m-(methylthio)benzoyl chloride (2-chloro-4-nitrophenyl)hydrazone,
m-(methylthio)benzoyl chloride (3-methyl-4-nitrophenyl)hydrazone,
m-(methylthio)benzoyl chloride [3-methyl-5-(trifluoromethyl)phenyl]hydrazone,
m-(methylthio)benzoyl chloride [p-(methylthio)phenyl]hydrazone,
m-(methylthio)benzoyl chloride [3-(methylthio)-5-(trifluoromethyl)phenyl]hydrazone,
m-(methylthio)benzoyl chloride (p-fluorophenyl)hydrazone, and
3-(methylthio)-5-(n-hexyl)benzoyl chloride [3,5-di-n-butyl-4-(methylthio)phenyl]hydrazone, respectively.

In the Formulas I and II, above, the substituent group "α-$F_n$alkyl" is an alkyl group of from 1 to 3 carbon atoms, inclusive, having the α-carbon substituted with fluorine atoms. More particularly the substituent group is trifluoromethyl α,α-difluoroethyl, and α, α-difluoropropyl. Similarly "alkylthio" means methylthio, ethylthio, isopropylthio, hexylthio, and the like.

The new arthropocidal ar or ar' (alkylthio)benzoyl chloride phenylhydrazones of Formula I can be used as the pure compounds, such as those described in the Examples, as technical grade compounds from commercial production, or as mixtures of individual pure compounds; but for practical reasons, the compounds are preferably formulated with a diluent carrier with or without adjuvants for use against arthropod pests. There are many different kinds of diluent carriers suitable for the method and formulation embodiments of this invention. Dispersible carriers are commonly used in the art. Such carriers may or may not include adjuvants such as wetting agents, emulsifying agents, stickers, and other components that indirectly promote efficacy.

For example, pesticidal formulations useful against arthropod pests which become epidemic can be formulated as dusts, wettable powders, emulsifiable concentrates, aqueous dispersions, solutions, and flowable creams for application to a situs, animals, and foliage, seeds or other parts of plants. Granular formulations can be prepared and applied to soil or on surfaces. Moreover, the new ar or ar' (alkylthio)benzoyl chloride phenylhydrazones of the invention can be the sole active agent in a formulation or other insecticidal, miticidal, fungicidal, virucidal, or bactericidal components may be included.

The new ar or ar' (alkylthio) benzoyl chloride phenylhydrazones can be readily formulated as dusts by grinding a mixture of the compound and a pulverulent carrier in the presence of each other. Grinding is conveniently accomplished in a ball mill, a hammer-mill, or by air-blast micronization. A suitable ultimate particle size is less than 60 microns. Preferably, a 95% of the particles are less than 50 microns, and about 75% are 5 to 20 microns. Dusts of that degree of comminution are conveniently free-flowing and can be applied to animals, inanimate matter, fruit trees, crop plants, and soil so as to effect thorough distribution and coverage. Dusts are particularly adapted for effectively controlling insects and mites over wide areas when applied by airplane. They are also indicated for application to the undersides of plant foliage and to the skin of poultry and hairy animals.

Representative suitable pulverulent carriers include the natural clays such as China, Georgia, Barden, attapulgus, kaolin, and bentonite clays; minerals in their natural forms as they are obtained from the earth such as talc, pyrophyllite, quartz, diatomaceous earth, fuller's earth, chalk, sulfur, silica and silicates; chemically modified minerals such as washed bentonite, and colloidal silica; and organic flours such as wood, walnut shell, soybean, cottonseed, and tobacco flours, and free-flowing, hydrophobic starches.

Dusts can also be prepared by dissolving an ar or ar' (alkylthio) benzoyl chloride phenylhydrazone in a volatile solvent such as methylene chloride, mixing the solution with a pulverulent carrier and evaporating the solvent.

The proportions of pulverulent carrier and ar or ar' (alkylthio) benzoyl chloride phenylhydrazone can vary over a wide range depending upon the arthropod pests to be controlled and the conditions of treatment. In general, dust formulations can contain up to about 90% (on a weight basis) of the active ingredient. Dusts having as little as 0.001% of the active ingredient can be used, but a generally preferred proportion is from about 0.50 to about 20% of active ingredient.

The dispersible powder formulations of this invention are prepared by incorporating a surfactant in a dust formulation prepared as described above. When about 0.1 to about 12% of a surfactant is incorporated in a dust, the dispersible powder thus obtained is particularly adapted for further admixture with water for spraying on inanimate matter and products, fruit trees, field crops, soil, and livestock. The dispersible powders can be admixed with water to obtain any desired concentration of active ingredient, and the mixture can be applied in amounts sufficient to obtain predetermined rates of application and uniform distribution. With this flexibility in mind, the dispersible powders of the invention can conveniently comprise preferably about 10 to about 80% of active ingredient.

Representative surfactants useful for preparing dispersible powder formulations of this invention include alkyl sulfates and sulfonates, alkyl aryl sulfonates, sulfosuccinate esters, polyoxyethylene sulfates, polyoxyethylenesorbitan monolaurate, alkyl aryl polyether sulfates, alkyl aryl polyether alcohols, alkyl naphthalene sulfonates, alkyl quaternary ammonium salts, sulfated fatty acids and esters, sulfated fatty acid amides, glycerol mannitan laurate, polyalkylether condensates of fatty acids, lignin sulfonates, and the like. The preferred class of surfactants includes blends of sulfonated oils and polyalcohol carboxylic acid esters (Emcol H-77), blends of polyoxyethylene ethers and oil-soluble sulfonates (Emcol H-400), blends of alkyl aryl sulfonates and alkylphenoxy polyethoxy ethanols (Tritons X-151, X-161, X-171), e.g., about equal parts of sodium kerylbenzene sulfonate and isooctylphenoxy polyethoxy ethanol containing about 12 ethoxy groups, and blends of calcium alkyl aryl sulfonates and polyethoxylated vegetable oils (Agrimul $N_4S$). It will be understood, of course, that the sulfate and sulfonate surfactants suggested above will preferably be used in the form of their soluble salts, for example, their sodium salts. All of these surfactants are capable of reducing the surface tension of water to less than about 40 dynes per centimeter in concentrations of about 1% or less. The dispersible powder formulations can be prepared with a mixture of surfactants of the types indicated if desired.

A suitable dispersible powder formulation is obtained by blending and milling 327 lbs. of Georgia Clay, 4.5 lbs. of isooctylphenoxy polyethoxy ethanol (Triton X-100) as a wetting agent, 9 lbs. of a polymerized sodium salt of substituted benzoid long-chain sulfonic acid (Daxad 27) as a dispersing agent, and 113 lbs. of the active ingredient. The resulting formulation has the following percentage composition (parts herein are by weight unless otherwise specified).

| | |
|---|---|
| Active ingredient | 25% |
| Isooctylphenoxy polyethoxy ethanol | 1% |
| Polymerized sodium salt of substituted benzoid long-chain sulfonic acid | 2% |
| Georgia Clay | 72% |

This formulation, when dispersed in water at the rate of 10 lbs. per 100 gals., gives a spray formulation containing about 0.3% (3000 ppm) active ingredient which can be applied to insects, spiders, ticks, or mites, plants or other arthropod habitats, or to their foods for control of various arthropod pests.

If desired, dispersants such as methyl cellulose, polyvinyl alcohol, sodium ligninsulfonates, and the like can be included in the dispersible powder formulations of this invention. Adhesive or sticking agents such as vegetable oils, naturally occuring gums, casein, and others can also be included. Corrosion inhibitors such as epichlorohydrin and anti-foaming agents such as stearic acid can also be included.

The new anti-arthropodal ar or ar' (alkylthio) benzoyl chloride phenylhydrazones of this invention can be applied to insects, spiders, ticks, mites, objects, or situs in aqueous sprays without a solid carrier. Since, however, the compounds themselves are relatively insoluble in water they are preferably dissolved in a suitable inert organic solvent carrier. Advantageously, the solvent carrier is immiscible with water so that an emulsion of the solvent carrier in water can be prepared. If, for example, a water-miscible solvent carrier such as ethanol is used the solvent carrier will dissolve in the water and any excess ar or ar' (alkylthio) benzoyl chloride phenylhydrazone will be thrown out of solution. In an oil-in-water emulsion, the solvent phase is dispersed in the water phase and the dispersed phase contains the active ingredient. In this way, uniform distribution of a water insoluble active ingredient is achieved in an aqueous spray. A solvent carrier in which ar or ar' (alkylthio) benzoyl chloride phenylhydrazones are highly soluble is desirable so that relatively high concentrations of active ingredient can be obtained. Sometimes, one or more solvent carriers with or without a cosolvent can be used in order to obtain concentrated solutions of the active ingredient, the main consideration being to employ a water-immiscible solvent for the active ingredient that will hold the compound in solution over the range of concentrations useful for applying to insects and mites.

The emulsifiable concentrates of the invention are prepared, therefore, by dissolving the active ingredient and a surfactant in a substantially water-immiscible solvent carrier (i.e., a solvent carrier which is soluble in water to the extend of less than 2.5% by volume at temperatures of the order of 20° to 30° C.), for example, cyclohexanone, methyl propyl ketone, summer oils, ethylene dichloride, aromatic hydrocarbons such as benzene, toluene, and xylene, and high-boiling petroleum hydrocarbons such as kerosene, diesel oil, and the like. If desired, a cosolvent such as methyl ethyl ketone, acetone, isopropanol, and the like can be included with the solvent carrier in order to enhance the solubility of the active ingredient. Aqueous emulsions are then prepared by mixing with water to give any desired concentration of active ingredient. The surfactants which can be employed in the aqueous emulsions of the invention are those types noted above. Mixtures of surfactants can be employed, if desired.

Advantageously, the concentration of active ingredient in the emulsifiable concentrates can range from about 5 to about 50% by weight, preferably from about 10 to about 40%. A concentrate comprising 20% (by weight) of the compound dissolved in a water-immiscible solvent of the kind noted above can be admixed with an aqueous medium in the proportions of 13 ml. of concentrate with 1 gal. of medium to give a mixture containing 700 parts of active ingredient per million parts of liquid carrier. Similarly, 1qt. of a 20% concentrate mixed with 40 gals. of water provides about 1200 ppm (parts per million) of active ingredient. In the same manner, more concentrated solutions of active ingredient can be prepared.

The concentrate formulations of the invention which are intended for use in the form of aqueous dispersions of emulsions can also comprise a humectant, that is to say, an agent which will delay the drying of the composition in contact with material to which it has been applied. Suitable humectants include glycerol, diethylene glycol, solubilized lignins, such as calcium ligninsulfonate, and the like.

The granular formulations of this invention are convenient for application to soil when persistence is desired. Granulars are readily applied broadcast or by localized, e.g., in-the-row applications. The individual granules may be any desired size from 10 to 60 mesh, advantageously 20 to 40 mesh. Granulars are prepared by dissolving the active compound in a solvent such as methylene chloride, xylene, or acetone and applying the solution to a quantity of a granulated absorbent carrier. Representative granulated absorbent carriers include ground corn cobs, ground walnut shells, ground peanut hulls, and the like. If desired, the impregnated granulated absorbent carrier can be coated with a coating that will preserve the integrity of the granular until it is applied to an object or situs favorable for release of the active ingredient.

The rates of application to insects, spiders, ticks, mites, objects, or situs will depend upon the species of arthropod to be controlled, the presence or absence of desirable living organisms, temperature conditions of treatment, and the method and efficiency of application. In general, arthropocidal activity is obtained when the compounds are applied at concentrations of about 10 to about 6000 ppm, preferably at concentrations of about 30 to about 4000 ppm.

The formulations containing new ar or ar' (alkylthio) benzoyl chloride phenylhydrazones according to the invention, can be applied to insects, mites, ticks, spiders, objects or situs by conventional methods. For example, an area of soil, a building, or plants can be treated by spraying wettable powder suspensions, emulsions, or solutions from power sprayers or from hand-operated knapsack sprayers. Dips can be used for livestock. Dusts can be applied by power dusters, or by hand-operated dusters. Creams and ointment formulations can be applied to skin or objects for prolonged protection from insects, spiders, ticks, or mites.

The active compounds of the invention can also be formulated in relatively dilute proportions in a dispersible insecticide carrier for household applications. Thus, the active compounds can be formulated in dusts having from about 0.1 to 5.0% active ingredient with a dusting powder as hereinbefore described, and in solutions containing from about 0.01 to about 5.0% active ingredient with deodorized kerosene for aerosol applications.

It will of course be appreciated that the conditions encountered when applying the method and formulations of this invention to actual practice can vary widely. Included among the variables that may be encountered are the degree of infestation by pests, the particular pest to be controlled, the particular situs being treated, the age or degree of development of animals or plants, the prevailing weather conditions, such as temperature, relative humidity, rainfall, dews, and so forth.

The compounds of Formula I are effective pesticides that can be used to control invertebrate pests in agriculture, in industry, and around the home. The compounds have been found to be active against invertebrate animals of the Phylum Arthropoda, illustratively Class Insecta, for example, order Coleoptera, more specifically, the cotton boll weevil (*Anthonomus gran-* dis Boheman), the confused flour beetle (*Tribolium confusum* Jacquelin de Val), and the Mexican bean beetle (*Epilachna varivestis* Mulsant), order Diptera, more specifically, the housefly (*Musca domestica* Linnaeus), order Orthoptera, more specifically, the house cricket (*Acheta domesticus* Linnaeus), and the German cockroach (*Blatella germanica* Linnaeus), and order Lepidoptera, more specifically, the Southern armyworm (*Prodenia eridania* Cramer), and Class Arachnida, for example, order Acarina, more specifically, the two-spotted spider mite (*Tetranychus urticae* Koch).

Efficacy against invertebrate pests has been demonstrated at concentrations of 1000, 500, 100, 50, and even 10 ppm depending upon the specific insect or mite used. Some invertebrate animal will be more sensitive to the compounds than others, and others might be quite resistant. In general, the compounds of Formula I are used at concentrations ranging from about 30 to about 6000 ppm.

Compounds of the invention have also shown activity against parasitic worms, e.g., *Nematospiroides dubius* and *Syphacia obvelata*. The compound p-(methylthio)-benzoyl chloride phenylhydrazone is particularly effective therefor.

I claim:

1. The chemical compounds ar or ar' (alkylthio) benzoic acid 2-phenylhydrazides having the structural formula:

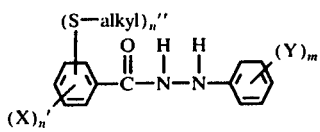

wherein "alkyl" is of from 1 to 6 carbon atoms, inclusive; X is halogen, alkyl of from 1 to 6 carbon atoms, inclusive, alkylthio of from 1 to 6 carbon atoms, inclusive, $\alpha$-$F_n$alkyl of from 1 to 3 carbon atoms, inclusive, wherein $n$ is the integer 2 or 3, and nitro; Y is alkyl of from 1 to 6 carbon atoms, inclusive, halogen, alkylthio of from 1 to 6 carbon atoms, inclusive, $\alpha$-$F_n$alkyl of from 1 to 3 carbon atoms, inclusive, and nitro; $n'$ is an integer 0 to 3, inclusive; $n''$ is 1 except when Y is alkylthio, when it can be zero; and $m$ is an integer from 0 to 3, inclusive, the sum of $n' + n'' + m$ being not more than 6, the sum of carbon atoms in the alkyl substituents being not more than 15, there being no more than one nitro group in the molecule, and no more than two $\alpha$-$F_n$alkyl groups on any benzene ring or three total.

2. Chemical compounds according to claim 1 wherein $n'$ is zero.

3. Chemical compounds according to claim 2 wherein $m$ is zero.

4. Chemical compounds according to claim 3 wherein "S-alkyl" is in the para position.

5. The chemical compound according to claim 4 p-(methylthio)benzoic acid 2-phenylhydrazide.

6. The chemical compounds according to claim 1 wherein $n''$ is one and "S-alkyl" is methylthio.

7. The chemical compounds according to claim 6 wherein $n'$ is zero.

8. Chemical compounds according to claim 1 wherein Y is alkylthio.

9. Chemical compounds according to claim 8 wherein $m$ is one.

10. Chemical compounds according to claim 9 wherein Y is in para position.

11. Chemical compounds according to claim 10 wherein Y is methylthio.

12. The chemical compound according to claim 11 benzoic acid 2-[p-(methylthio)phenyl]hydrazide.

* * * * *

UNITED STATES PATENT AND TRADEMARK OFFICE
CERTIFICATE OF CORRECTION

PATENT NO. : 4,014,932

DATED : March 29, 1977

INVENTOR(S) : Girts Kaugars

It is certified that error appears in the above—identified patent and that said Letters Patent is hereby corrected as shown below:

Column 7, line 52, "3,5-din-butyl" should read -- 3,5-di-n-butyl --.

Column 9, line 37, "2-(p-" should read -- 2-[p- --.

Column 15, line 5, "Orthopetera" should read -- Orthoptera --.

Column 15, line 16, "animal will" should read -- animal pests will --.

Signed and Sealed this

Fifth Day of January 1982

[SEAL]

Attest:

Attesting Officer

GERALD J. MOSSINGHOFF

Commissioner of Patents and Trademarks